United States Patent [19]
Koenig

[11] Patent Number: 5,492,835
[45] Date of Patent: Feb. 20, 1996

[54] SWAB IDENTIFICATION TESTING DEVICE AND METHOD

[75] Inventor: Don Koenig, Atlanta, Ga.

[73] Assignee: Gerald J. Churchill, Atlanta, Ga.

[21] Appl. No.: 274,418

[22] Filed: Jul. 13, 1994

[51] Int. Cl.⁶ .......................... G01N 33/20; G01N 33/32
[52] U.S. Cl. ................... 436/77; 422/58; 422/61; 435/810
[58] Field of Search ................. 436/77; 422/56–58, 422/61, 100; 435/34, 805, 810

[56] References Cited

U.S. PATENT DOCUMENTS

| | | | |
|---|---|---|---|
| 3,642,450 | 2/1972 | Eriksson | 422/61 |
| 3,965,888 | 6/1976 | Bender | 422/58 X |
| 4,559,949 | 12/1985 | Levine | 436/66 X |
| 5,010,020 | 4/1991 | Gould | 436/77 |
| 5,039,618 | 8/1991 | Stone | 436/77 |

*Primary Examiner*—Lyle A. Alexander
*Attorney, Agent, or Firm*—Dowell & Dowell

[57] ABSTRACT

A testing apparatus and method for the immediate testing of painted surfaces to determine the type of paint and/or presence of mildews or lead wherein the apparatus includes an outer resealable wrapper and at least one test packet including a secondary swab saturated with a first predetermined substance and a primary swab saturated with a second predetermined substance. The primary swab has an adhesive border which permits the test pouch to be temporarily adhered to a surface being tested.

18 Claims, 1 Drawing Sheet

SWAB IDENTIFICATION TESTING DEVICE AND METHOD

BACKGROUND OF THE INVENTION

1. Field of the Invention

This invention is generally directed to methods and devices for testing painted surfaces to detect the type of paint, i.e. oil or water base, and presence of mildew or lead in or on the painted surface. More particularly, the invention is directed to reliable, environmentally safe and economically disposable swabs or packets which include opposing impregnated patches or pads at least one of which is surrounded by adhesive areas. The packets are retained within a non-porous airtight and resealable wrapper until opened for use. Once used, the opposing pads are closed upon one another for disposal and are retained closed by the adhesive areas surrounding one of the pads. The used packets may further be sealed for disposal in the resealable wrapper or pouch.

2. History of the Related Art

It is extremely important in preparing to repaint previously coated surfaces such as walls, ceilings, doors and window frames in both domestic and commercial structures, what type of existing coating is present, i.e. whether the previously applied paint is an oil base or water base paint. The type of existing paint will dictate what types of coatings can be applied over the existing painted surfaces and/or what additional preparation, treatment or replacement of the existing surface materials may be necessary. Currently there are no readily available or reliable consumer products which permit tests to be quickly, easily and economically made to determine what type of paint is present and whether or not lead or mildew may be present. If lead or mildew is present, surfaces must be replaced or treated prior to repainting.

U.S. Pat. No. 5,039,618 to Stone discloses a test swab cartridge and method for detecting lead and cadmium in paint. However, the use of a cartridge device requires the breaking of an internal cartridge to allow reagents to mix with fillers. In some instances, the reference discloses two internal cartridges which must be broken so that the reagents therein are mixed before the swabs can be used to test surfaces for lead or cadmium. The problem with these approaches is that they require an excess amount of reagents. Due to the strong acidic nature of some reagents, such devices are potentially toxic and hazardous to individuals.

U.S. Pat. No. 3,974,678 describes a testing device used to "determine the cure of a film or the like on a test panel." The tester is composed of a clamp for holding the panel to be tested, a weight to be placed on the panel, a quantity of absorbent material secured to the weight and a drive mechanism including an elongated reciprocally shiftable member having a distal end at which the weight is attached. The absorbent material is saturated with a supply of a predetermined chemical, corresponding to the test for which the cure of the film is to be determined. A control element is provided to cause a repetitious rubbing action on the film. As can be seen, this testing method is very complex and expensive due to the cost of equipment, setup time and the time to perform a test.

In direct contrast to the case of such limited prior art for testing for paint, the prior art for mildew testing is filled with various agents, substances or chemicals which are used to identify, remove or eliminate mildew. However, many of the agents, substances or chemicals have major shortcomings, including from at least one to almost all of the following unfavorable characteristics: very toxic, difficult to use, complex in composition, relatively expensive, requires special handling, requires special storage procedures or containers, requires special disposal procedures.

Other testing methods and procedures require access to a variety of chemical agents, cloths, wiping pads and other materials, the use of which are not practical and/or potentially hazardous. Also, prior art testing methods have not adequately addressed the need for safe disposal of testing chemicals and materials.

SUMMARY OF THE INVENTION

The test swab packets in the preferred embodiment are adhered or sealed about their periphery and include a first inner surface having a test pad material secured thereto which is substantially bordered by an adhesive area which is used to secure the test patch against a painted surface. The other portion of the inner surface of the packet is utilized as a covering surface and in some instances may include a second testing or cleaning pad material which is protected and isolated from the opposite test pad by a film or covering mounted therebetween. In the preferred embodiment, the two sections of the patch are in opposing relationship with respect to one another and are separable along at least three sides by partially perforated edges. Once used, the sides of the packets are folded upon one another and are retained closed by the adhesive areas adjacent one of the test pads. In some embodiments, the packets may be provided with a flange or strip for facilitating opening of the two sides of the packets.

The test pad areas of the swab packets may be impregnated with an isopropyl rubbing alcohol when used to determine whether or not an existing paint is a water base or oil base paint. If a test is being conducted to determine the presence of lead, the test pad will be impregnated with a substance which changes color in response to the presence of lead such as citric acid. In those instances where the swabs are being utilized to test for mildew, the pad may be impregnated with a household bleach.

In practicing the invention, the packets are opened to expose the impregnated test pads and thereafter the packets are adhered utilizing the adhesive material surrounding one of the test pads to the surface to be tested. Depending upon whether the test is being made for mildew, lead or the type of paint, i.e. water base or oil base, the pad will remain secured to the wall for different periods of time up to approximately 15 minutes. Once a test has been completed, a change in color of the pads will give the appropriate indication as to what substance or type of paint are present. Thereafter, and without having to contact the impregnated test pad areas, the swab packets are closed upon themselves and are retained closed by the adhesive strips associated therewith.

It is the primary object of the present invention to provide economical and simple testing devices and methods for determining the existing paint coatings on surfaces including walls, ceilings, doors and window frames without having to expose an individual to contact with a testing reagent chemical or toxic substance.

It is yet another object of the present invention to provide testing swabs and testing devices for determining the presence of lead or mildew and or determining the type of paint applied to a surface which includes a packet having an adhesive strip associated therewith for mounting the testing swab against the surface to be tested and which, after a test is made, allows the swab to be closed upon itself for safe disposal.

It is yet a further object of the present invention, to provide a testing device which may be economically made available for use by individuals, including homeowners, so that tests can be easily made with respect to determining whether or not lead is present on a surface so that steps may be taken to have the lead sealed or removed prior to repainting a given surface area.

It is a further object of the present invention to provide a swab testing device which may be readily disposed in a safe manner and which is usable without having to expose an individual to contact with a chemical agent and which will give generally immediate results with respect to indicating the presence of lead, mildew or the type of paint coating a particular surface.

DESCRIPTION OF THE PREFERRED EMBODIMENT

Figure 1:
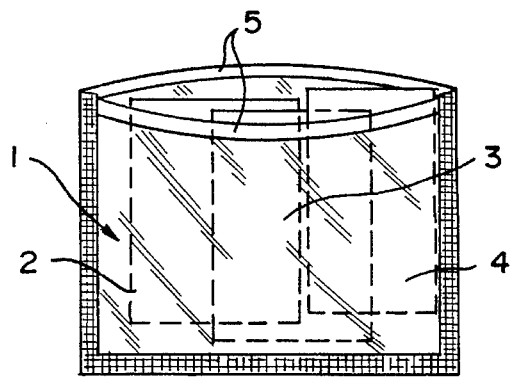
FIG. 1 is a front perspective view of a pouch for enclosing testing swab packets of the present invention.

Reference will now be made to the preferred embodiment of the invention. With reference to the drawings, FIG. 1 illustrates a first embodiment including an outer wrapper or bag-like container 1 used to hold the various types of identification testing swabs. The wrapper includes an adhesive resealing strip 5 which, after the test swabs have been used, provides for a simple, safe and quick disposal container for the swabs.

Shown in FIG. 1 are the three specific identification test swab packets covered in this preferred embodiment of the invention: the swab packet for testing for the presence of water base paint 2, the swab packet for testing the presence of mildew 3, and the swab packet for testing for the presence of lead 4.

Figure 2:
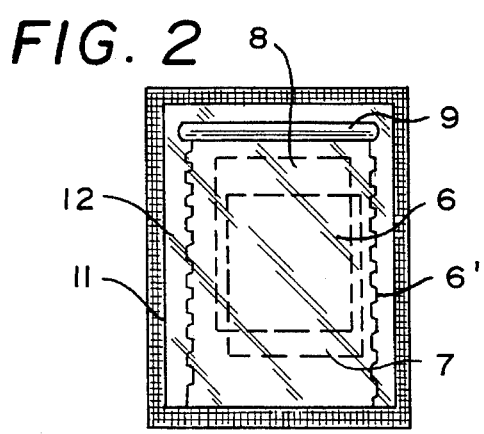
FIG. 2 is a front elevational view of a testing swab packet of the present invention in a closed configuration.

Each test swab packet, as shown in FIG. 2, includes front and rear portions having edges 11 which are adhered or sealed to each other. The front of the packet has a tear open flap 6 with a pull tab 9 which allows access to a primary test pad 8 and a secondary test pad 7 which are contained within the packet. The secondary pad 7 is attached to the inside front of the tear open flap 6 and the primary pad 8 is attached to the inside of the rear portion of the airtight packet. Lines of weakness 6' are provided in the front portion to facilitate separation of the flap 6. Such lines are provided along the upper and side portions of the front portion of the packet. It is preferred that the flap remain connected to the front cover along the lower edge.

The two pads are saturated with a predetermined substance depending on the type of test and the method to be used. For example, the primary swab pad 8 could contain a reagent and the secondary swab pad 7 a filler, or the secondary swab pad 7 could contain a cleaning compound and the primary swab pad 8 a mild acid.

To determine the presence of water base paint, the user first wipes the secondary swab pad 7 across a small area of the surface being tested in order to clean the test area. Next the user wipes the primary swab pad 8, across the same test area. The user visually observes the surface of the test swab pad 8. If the swab pad contains paint pigment of the same color as the surface being tested, the test is positive and the paint on the surface tested is water base. If there is no paint pigment on the test swab pad 8 the test is negative and the paint on the surface is non-water base. In this embodiment, both the secondary swab pad 7 and the primary swab pad 8 are impregnated with a common household chemical, isopropyl alcohol, which is non-toxic and completely safe to use, as the predetermined saturating substance.

To determine the presence of mildew, both the primary swab pad 8 and the secondary swab pad 7 can be used as primary pads 8. Both are saturated with household bleach, which is non-toxic and completely safe to use, as the predetermined saturating substance. This allows the user to test two separate surfaces, or to test two separate areas on the same surface for the presence of mildew. The test swab pad 8 is first dabbed or tapped—but not rubbed—on a test area where there is a foreign substance that looks like dirt or mildew. After several minutes, the user makes a visual inspection of the test area. If the test is positive, a black, green or brown substance on the surface being tested will have vanished or will have changed color dramatically, indicating the presence of mildew. If the test is negative, there will be little or no observable change to the substance on the tested surface area, indicating the absence of mildew.

Figure 3:
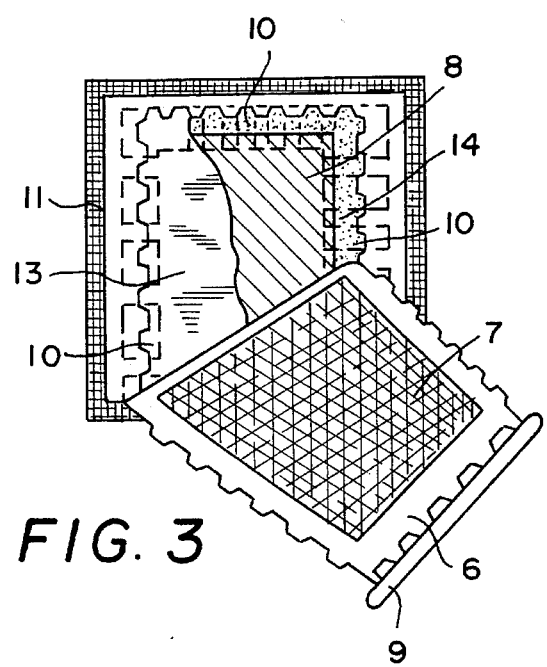
FIG. 3 is a front elevational view of the swab packet of FIG. 2 shown in open configuration having two testing pads, one surrounded by an adhesive strip.
Figure 5:
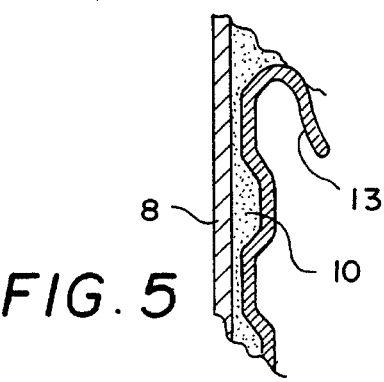
FIG. 5 is an enlarged partial cross sectional view of the primary pad and covering material of the swab packet of FIG. 3.
Figure 6:
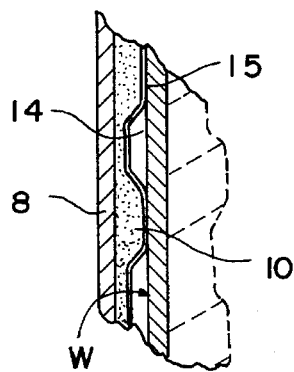
FIG. 6 is an enlarged cross sectional view of the embodiment of FIG. 5 showing the pad secured to a surface being tested.
Figure 4:
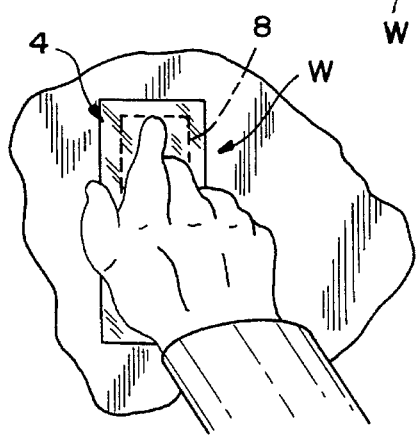
FIG. 4 is an illustrational view showing the testing swab of FIG. 3 being applied to a surface area.

With reference to FIG. 3, when the airtight packet is opened using the pull tab 9 to open the tear open flap 6, the secondary swab pad 7 which is attached to the tear open flap 6, is exposed. The primary swab pad 8 is sealed and covered by a protective film 13 as illustrated in FIG. 4. The primary swab pad 8 has an adhesive 10 around it's periphery which is a means of holding the swab pad to the test surface, in a vertical, horizontal or inverted position for a predetermined amount of time dependent on the predetermined acidic or other saturated substance used in the primary swab pad 8. As illustrated in FIGS. 5 and 6, the primary swab pad 8 includes projections 15 that form air channels 14 to allow air to get to a test surface such as a wall "W".

In testing for lead, the user makes a small scratch, deep enough to penetrate all of the layers of surface coatings on the material being tested. If there is a surface coating such as a glaze on pottery, a small chip is made to remove the glaze. The secondary swab pad 7 is applied to the test area to remove dirt and other substances. Next, the primary swab pad 8 is stuck to the test area in contact with the scratch by means of the adhesive 10, as shown in FIGS. 5 and 6. Due to the air channel vents 14, oxygen can reach the test area under the primary swab pad 8. The primary swab pad 8 is left in place for a predetermined period of time, such as 15 minutes. Thereafter, the primary swab pad 8 is removed from the test surface and visually inspected. If there is a color change on the surface of the test swab pad 8, the test is positive and indicates the presence of lead in one of the layers of coatings on that surface. If the color on the surface of the test swab is unchanged, the test is negative.

In this embodiment, the secondary swab pad 7 is impregnated with a common household chemical, isopropyl alcohol, which is non-toxic and completely safe to use, as the predetermined saturating substance. The primary swab pad 8 is impregnated with a mild acid, such as citric acid, which is non-toxic and safe for the user.

Both the primary swab pad 8 and secondary swab pad 7, as presented in the drawings contained herein, are shown to have as their relative shape a square or rectangle for the purposes of illustration. However, in actual use, the swabs will have any shape including but not limited to: circles, triangles, trapezoids and irregular shapes. Once a test has been completed, the two sections supporting the test pads are folded upon one another and adhered to one another by the adhesive 10. The adhesive layer will seal any chemical reagent or material removed during the test process. This permits the safe disposal of the chemical reagent and any lead which may have been detected without allowing the materials to be touched by an individual's hand. It is preferred to thereafter place the used packets in the exterior pouch for further safety.

The present invention provides a very safe, economical and readily disposable testing device for indicating the presence of mildew or lead on a painted surface and also for determining the type of paint, i.e. either water base or non-water base, which has been applied to the surface. By determining the types of paints and the potential for problems with mildew and lead, the safe covering, repainting, papering or other treatment of a previously covered surface may be undertaken without detrimental results.

The foregoing description of the preferred embodiments of the invention has been presented to illustrate the principles of the invention and not to limit the invention to the particular embodiments illustrated. It is intended that the scope of the invention be defined by all of the embodiments encompassed within the following claims, and their equivalents.

I claim:

1. A swab device for testing characteristics of a painted surface, comprising a packet having first and second sections, each of said first and second sections having inner and outer surfaces, said first and second sections being closed relative to each other in a pre-use condition so that said inner surfaces are in a respective opposing relationship, a first test pad mounted to said inner surface of one of said first and second sections of said packet, a first chemical testing substance effective for a testing characteristic of a painted surface being impregnated within said first test pad, and adhesive means on said inner surface of one of said first and second sections for securing said first and second sections substantially in said opposing relationship with said first test pad being contained therebetween after said first and second sections have been opened relative to one another and said first test pad has been used on a painted surface.

2. The swab device of claim 1 wherein said adhesive means at least partially surrounds said first pad.

3. The swab device of claim 2 wherein each of said first and second sections have peripheral edges, said second section having a central portion which is severable relative to the peripheral edges thereof along a line of weakness formed in said second section.

4. The swab device of claim 3 including a tab extending from said central portion of said second section.

5. The swab device of claim 3 including a second testing pad mounted to said inner surface of the other of said first and second sections, and a second chemical impregnated within said second pad.

6. The swab device of claim 5 including means separating said second pad from said first pad to prevent any cross contamination of said first and second chemicals.

7. The swab device of claim 6 including a pouch for enclosing said packet and seal means for closing said pouch in air-tight relationship about said packet.

8. The swab device of claim 2 including a second testing pad mounted to said inner surface of the other of said first and second sections, and a second chemical impregnated within said second pad.

9. The swab device of claim 8 including film means separating said second pad from said first pad to prevent any cross contamination of said first and second chemicals.

10. The swab device of claim 8 including a pouch for enclosing said packet, and seal means for closing said pouch in air-tight relationship about said packet.

11. The swab device of claim 2 including a pouch for enclosing said packet, and seal means for closing said pouch in air-tight relationship about said packet.

12. A method of testing paint on a surface comprising the steps of: providing a packet having a test pad sealed in air-tight relationship therein, said test pad being impregnated with a chemical testing substance effective for testing a characteristic of a painted surface, opening said packet to expose said test pad, adhering said test pad to a painted surface and allowing said test pad to remain in contact with the painted surface for a predetermined time, and removing the test pad from the painted surface and visually inspecting either the test pad or painted surface for a change of coloration indicating a characteristic of the painted surface.

13. The method of claim 12 further comprising subsequent to the step of visually inspecting, folding the test packet upon itself and adhesively closing the test pad in the packet and disposing of the packet.

14. The method of claim 12 wherein said chemical testing substance is isopropyl alcohol.

15. The method of claim 12 wherein said chemical testing substance is bleach.

16. The method of claim 12 wherein said chemical testing substance changes color in response to contact with lead.

17. The swab device of claim 2 wherein said first pad includes spaced raised surface portions which define air passages when said first pad is positioned against the painted surface.

18. The swab device of claim 8 wherein said first pad includes spaced raised surface portions which define air passages when said first pad is positioned against the painted surface.

\* \* \* \* \*